(12) United States Patent
Ay-Becker et al.

(10) Patent No.: US 12,150,794 B2
(45) Date of Patent: Nov. 26, 2024

(54) EXPANDING HOLDER AND TOOL SET

(71) Applicant: Aesculap AG, Tuttlingen (DE)

(72) Inventors: Eda Ay-Becker, Mengen (DE); Timo Knittel, Wurmlingen (DE)

(73) Assignee: Aesculap AG, Tuttlingen (DE)

(*) Notice: Subject to any disclaimer, the term of this patent is extended or adjusted under 35 U.S.C. 154(b) by 0 days.

(21) Appl. No.: 18/281,424

(22) PCT Filed: Mar. 8, 2022

(86) PCT No.: PCT/EP2022/055882
§ 371 (c)(1),
(2) Date: Sep. 11, 2023

(87) PCT Pub. No.: WO2022/189427
PCT Pub. Date: Sep. 15, 2022

(65) Prior Publication Data
US 2024/0148461 A1    May 9, 2024

(30) Foreign Application Priority Data
Mar. 12, 2021   (DE) ..................... 10 2021 106 110.5

(51) Int. Cl.
*A61B 50/20* (2016.01)
*A61B 50/33* (2016.01)

(52) U.S. Cl.
CPC .............. *A61B 50/20* (2016.02); *A61B 50/33* (2016.02)

(58) Field of Classification Search
CPC ......... A61B 50/20; A61B 50/22; A61B 50/24; A61B 50/30; A61B 50/33

USPC ................................................. 206/363, 370
See application file for complete search history.

(56) References Cited

U.S. PATENT DOCUMENTS

| | | | |
|---|---|---|---|
| 7,135,031 B2 | 11/2006 | Flint | |
| 9,877,765 B2 | 1/2018 | Barth et al. | |
| 11,278,373 B2 | 3/2022 | Zieris et al. | |
| 11,672,638 B2* | 6/2023 | Stoller | A61B 17/155 206/370 |
| 2010/0001152 A1 | 1/2010 | Golle et al. | |
| 2011/0139651 A1* | 6/2011 | Fujii | A61C 5/44 206/369 |

(Continued)

FOREIGN PATENT DOCUMENTS

| | | |
|---|---|---|
| CN | 1638698 A | 7/2005 |
| CN | 104602623 A | 5/2015 |

(Continued)

OTHER PUBLICATIONS

Office Action received in European Application No. 22 713 607.4-1113 dated Dec. 15, 2022, with translation, 9 pages.

(Continued)

*Primary Examiner* — Jacob K Ackun
(74) *Attorney, Agent, or Firm* — Christopher A. Rothe; CM Law

(57) ABSTRACT

A tool set includes an expander holder for plug-in holding of surgical tools and a retaining device. The expander holder includes a catching base formed by a flat, chamfer-free plate. Clamping arms for holding a tool to be inserted extend axially from the plate. The plate forms a welding, soldering or gluing portion in a central region on one or more flat sides of the plate.

10 Claims, 6 Drawing Sheets

(56) References Cited

U.S. PATENT DOCUMENTS

| | | | | |
|---|---|---|---|---|
| 2015/0122682 A1* | 5/2015 | Kerboul | ............... | B65D 25/108 |
| | | | | 206/370 |
| 2016/0144118 A1* | 5/2016 | Solomon | ................. | A61M 5/30 |
| | | | | 206/370 |
| 2017/0143449 A1 | 5/2017 | Zieris et al. | | |
| 2018/0271632 A1* | 9/2018 | Berg | ........................ | A61C 3/04 |
| 2018/0368932 A1* | 12/2018 | Krensky | ................ | A61B 50/20 |
| 2019/0223981 A1 | 7/2019 | Zieris et al. | | |
| 2022/0125603 A1* | 4/2022 | Huff | ...................... | A61F 2/3859 |

FOREIGN PATENT DOCUMENTS

| | | | |
|---|---|---|---|
| DE | 2713094 A1 | 10/1978 |
| DE | 102014109197 A1 | 1/2016 |
| EP | 0263011 A1 | 4/1988 |
| EP | 0916406 A2 | 5/1999 |
| EP | 3289987 A1 | 3/2018 |
| EP | 3164095 B1 | 3/2019 |
| WO | 2020078745 A1 | 4/2020 |

OTHER PUBLICATIONS

Search Report received in German Application No. 10 2021 106 110.5 dated Dec. 17, 2021, with translation, 11 pages.
Search Report received in International Application No. PCT/EP2022/055882 dated Jul. 5, 2022, with translation, 6 pages.
Written Opinion received in International Application No. PCT/EP2022/055882 dated Jul. 5, 2022, with translation, 12 pages.
Office Action received in Chinese Application No. 202280020746.1 dated Jan. 4, 2024, with translation, 12 pages.

\* cited by examiner

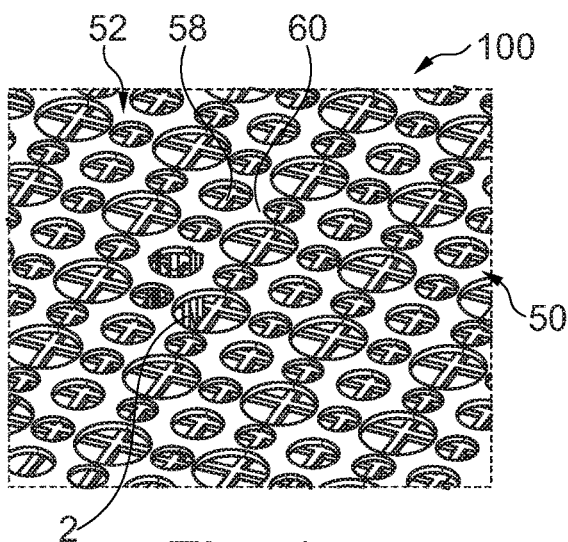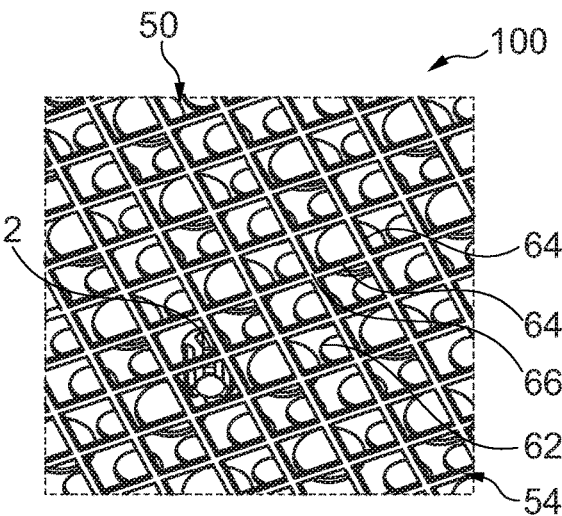
Fig. 1  Fig. 2
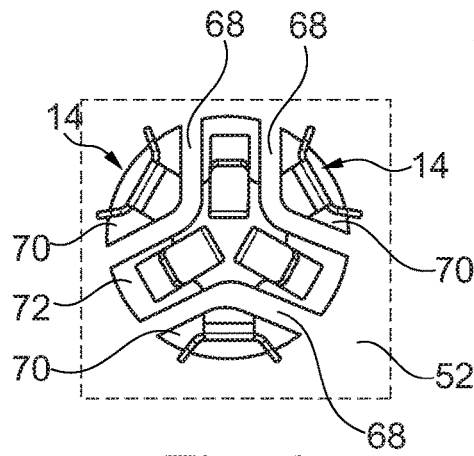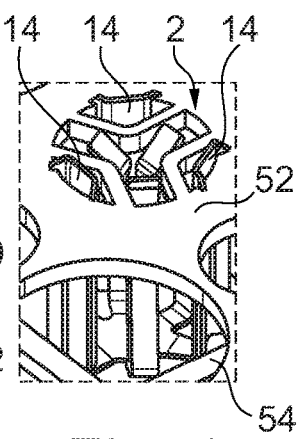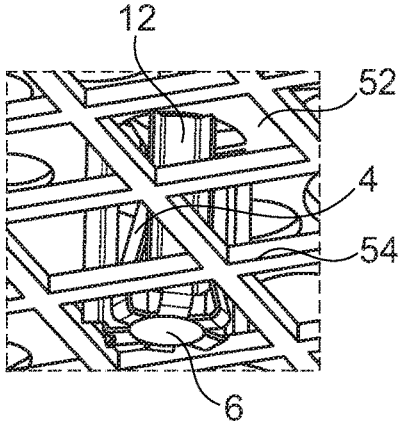
Fig. 3  Fig. 4  Fig. 5
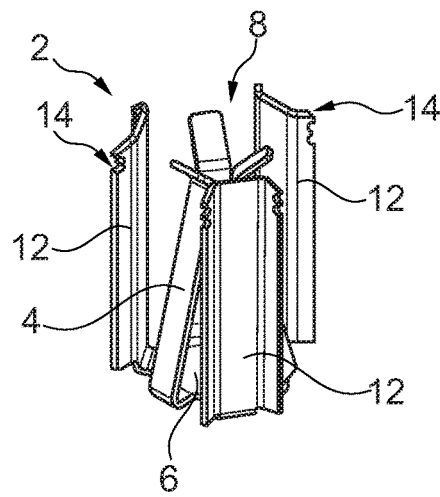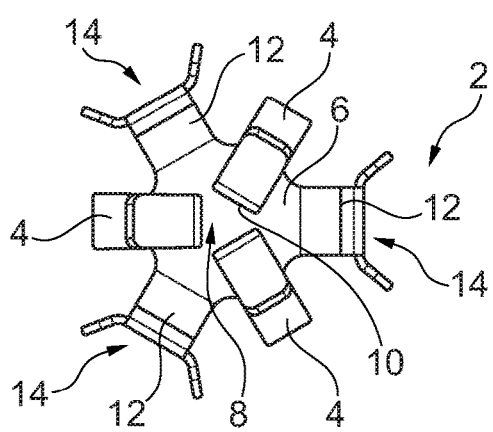
Fig. 6  Fig. 7

EXPANDING HOLDER AND TOOL SET

CROSS-REFERENCE TO RELATED APPLICATIONS

This application is the United States national phase entry of International Application No. PCT/EP2022/055882, filed on Mar. 8, 2022, and claims priority to German Application No. 10 2021 106 110.5, filed on Mar. 12, 2021. The contents of International Application No. PCT/EP2022/055882 and German Application No. 10 2021 106 110.5 are incorporated by reference herein in their entireties.

FIELD

The present disclosure relates to an expander holder of a tool set for plug-in holding of surgical tools, and a tool set comprising the expander holder and a retaining device.

BACKGROUND

In modern surgery, a large number of different instrument heads/tools are used, such as drilling or milling tools (with tool shaft), each of which can be detachably plugged onto/inserted into a handpiece with an instrument drive/motor. This allows the surgeon to change the instrument shaft with distal instrument head/effector inserted/inserted on/in the handpiece during operation of the handpiece, depending on the requirements of the application. In order to provide the operator with the easiest possible access to these instrument heads (hereinafter referred to as tools), the tools are usually stored in an orderly fashion in a surgical tool set, as is also known from the trade, for example, for drill sets. However, in order to avoid damage to the tools and to ensure that a required tool can be found quickly, the tools are not stored loosely, but are accommodated in expander holders in a fixing/clamping manner, which in turn are inserted into or fixed in a perforated matrix of the tool set (in the simplest case a perforated plate).

In this way, the individual tools are lined up coaxially/parallel to each other.

Conventional tool sets of this type for the storage of surgical tools belong to the general state of the art. These known tool sets essentially have a first perforated plate (a so-called sleeve sheet), which is formed as a usually metallic plate with a perforated matrix of round holes of different sizes. Expander holders for holding tools are inserted into or fixed in the holes. The expander holders each have an insertion opening for a specific surgical tool. Surgical tools have a distal tool engaging portion and a proximal shaft portion, and expander holders with different diameters of tool receiving openings allow tools with different shaft diameters to be properly and accurately seated. Additionally, the tool set may include a second perforated plate (a so-called bottom plate) connected to the first perforated plate, spaced parallel to the first perforated plate and limiting an insertion depth of the surgical tools.

In addition to the gentle storage of surgical tools, the thorough cleaning and sterilization of surgical tools is of utmost importance. Conventional expander holders are designed as a solid plastic sleeve with an elastically radially expandable inlay, which holds the tool inserted in it securely, but makes it difficult or even impossible for cleaning liquids or gases to flow around the tools stored in it.

To improve the flow around the tools, an expander holder is known from EP 3 154 095 B1, for example, which has a hollow plastic body with radial apertures and inwardly projecting filigree clamping arms, preferably made of plastic or metal, inserted inside the hollow body. The comparatively solid hollow plastic body is used to attach the expander holder to a holding device with a perforated plate, whereas the filigree clamping arms are used for point-like contacting of the tool inserted in the expander holder with the smallest possible contact surface.

Although these known expander holders are characterized by a high degree of stability, they still have the disadvantage that the hollow plastic body has radial apertures to allow the cleaning fluid to penetrate and rinse around it, but it is still possible that, for example, tissue residues and similar impurities can collect on the expander holder.

Another major disadvantage of these known expander holders is that the hollow plastic bodies are expensive and complex to manufacture, assemble and mount. In order to withstand high temperatures during sterilization, the plastic parts must be made of special temperature-resistant plastic, which increases manufacturing costs. To meet this medical requirement, the material PEEK is often used, which as such is cost-intensive, difficult to process and has a limited service life. In addition, a multi-part design of the expander holder, in particular with the hollow plastic body and the metal clamping arms embedded or inserted therein, requires the individual components to be assembled by hand. This is not only time-consuming, but also involves the risk of damage to the expander holders or incorrect assembly during assembly. In addition, contamination often sticks to plastic longer than to other materials such as metal due to its positive surface charge, which makes cleaning the expander holders even more difficult. The solid structure of conventional tool sets and their plastic production material also prove to be disadvantageous when drying the tool set after cleaning.

However, the metal clamping arms of the tool set and expander holders known in the prior art, which are inserted into the hollow plastic body, cannot be attached to the retaining device of the known tool set without the hollow plastic body, or cannot be attached in a stable manner.

SUMMARY

Thus, it is the object of the present disclosure to provide an expander holder of a tool set as well as a tool set which are simple and inexpensive to manufacture, ensure efficient cleaning and/or sterilization, and enable a simply constructed and at the same time stable attachment of the expander holder to a retaining device of the tool.

The core of the disclosure therefore consists in the fact that the expander holder, in addition to the clamping arms for holding a tool to be inserted, has the plate-shaped and, apart from the clamping arms, chamfer-free catching base in the axial direction, which forms a preferably metallic, in particular weldable, welding, soldering or gluing portion in its central region of at least one of its flat sides for direct firmly bonded attachment to the retaining device. In addition, the retaining device of the tool set is characterized in that, in contrast to the retaining devices of the prior art, the holes of two perforated plates connected to one another at a distance are arranged offset from one another so that the holes of a first perforated plate for inserting the tools are aligned with material between the holes of the second perforated plate in order to be able to attach the catching base to the material of the second perforated plate in a firmly bonded manner, in particular by welding.

More precisely, the expander holder is used for the plug-in, in particular vertical, holding of surgical tools. The expander holder has a number of circumferentially spaced, elastically deformable clamping arms, which form an insertion opening for the insertion of a tool on an open front side of the expander holder and have radially inwardly projecting engagement portions for force-fitting and/or form-fitting contacting of the tool for holding the tool. The clamping arms can preferably be made of metal and be arranged equally distributed in the circumferential direction of the expander holder. In addition, the expander holder has a preferably metallic catching base which is formed at an end portion of the expander holder opposite the insertion opening and from which the clamping arms extend in the axial direction towards the open front side. Preferably, the clamping arms can be formed on the catching base. The catching base can be used to limit the insertion depth of the tool to be inserted.

According to one aspect of the disclosure, the catching base of the expander holder for direct firmly bonded attachment of the expander holder to a retaining device of the tool set, preferably having a perforated plate, is formed by a preferably flat or curved chamfer-free plate from which exclusively the clamping arms extend axially, i.e. in a direction perpendicular to the plate, and which forms a welding, soldering or gluing portion in a central region on its one or both flat sides. This means that only the clamping arms protrude from the catching base, so that the catching base can be placed flat against the retaining device and fastened to it. This has the advantage that there is no need for a separate fastening device or one formed on the expander holder, so that there is no need to mount the fastening device on the clamping arms, while at the same time ensuring secure and stable fastening of the expander holder by means of a material bond via the welding, soldering or gluing portion formed on the catching base.

According to a preferred embodiment, a lower side of the catching base facing away from the insertion opening and/or an upper side of the catching base facing the insertion opening can form the preferably metallic welding, soldering or gluing portion, which is adapted and provided for the direct firmly bonded, in particular (spot) welding, attachment of the expander holder to the retaining device of the tool set. If the welding, soldering or gluing portion is formed on the lower side, the expander holder can easily be placed axially from above (in the insertion direction of the tool to be inserted) on the retaining device and firmly bonded thereto. If the welding, soldering or gluing portion is formed on the upper side, the expander holder can easily be placed axially from below (against the insertion direction of the tool to be inserted) on the retaining device and firmly bonded thereto.

According to a preferred embodiment, the expander holder can be adapted and provided in such a way that it can be inserted onto the perforated plate of the retaining device, having holes, against an insertion direction of the tool to be inserted, so that the clamping arms pass/reach through the holes and the catching base projects axially from the perforated plate as a spacer. The holes can preferably be round or star-shaped. In other words, the perforated plate can thus be kept at a distance from, for example, a receiving box into which the perforated plate is inserted in the insertion direction of the tool. This means that a lower side of the perforated plate can be kept axially spaced from the receiving box by the thickness of the catching base, so that flushing with cleaning fluid is improved.

According to a preferred embodiment, the catching base can have a weldable insert (/inlay) or a weldable coating. The weldable insert can, for example, be integrated as a circular or annular plate in the central region of the catching base. This has the advantage that the catching base or the expander holder as a whole can be made of a non-weldable material and still allow weldable attachment of the expander holder.

In accordance with an advantageous further development of the preferred embodiment, the clamping arms and the catching base can be formed in one piece from a bending elastic metal, preferably a spring steel, for example from the material 1.4310. The metal design allows the expander holder to be cleaned and sterilized particularly efficiently.

According to a preferred embodiment, the expander holder can be designed as a bending forming part. This allows the expander holder to be manufactured as a whole in a particularly simple and cost-effective manner, preferably from a metallic material. The one-piece design means that no additional assembly steps are necessary to assemble several individual parts.

More precisely, the tool set is used for plug-in holding of surgical tools. The tool set comprises the expander holder described above and a retaining device having a first perforated plate with first preferably round holes for insertion of a tool and a second perforated plate spaced parallel thereto and connected to the first perforated plate with second holes separated from each other by second crosspieces. The second crosspieces intersect at junction points aligned with the first holes, and the catching base of the expander holder is firmly bonded or bondable, in particular welded or weldable, to the junction points of the second crosspieces. The fact that the first holes are aligned with the second crosspieces forms a suitable contact surface and firmly bonded fastening surface for the catching base when the expander holder is inserted into the retaining device through the first holes in the insertion direction of the tool to be inserted.

According to a preferred embodiment, the second crosspieces can form a welding, soldering or gluing surface at the junction points that is at least as large as an area of the catching base, in particular as the welding, soldering or gluing portion of the catching base. This ensures that the expander holders are attached or can be attached to the second perforated plate over a (large) area.

According to a preferred embodiment, the second holes may be substantially rectangular, in particular square, in shape and arranged in rows offset by 60°. This means that the second holes are separated from each other by the second crosspieces intersecting at the junction points in a T-shape. According to the preferred embodiment, the second crosspieces can widen in such a way that they preferably curve convexly towards the hole center at the corner points of the second holes. That is, at the junction points of two crosspieces, (quarter-circular) material of the perforated plate is present at the angle enclosed by the crosspieces, reducing the cross-section of the second holes. This results in an essentially square shape of the second holes, the corner points of which curve inwards in an approximately quarter-circle shape. On the one hand, this has the advantage that a sufficiently large area is formed for the firmly bonded attachment of the expander holders to the junction points. The centrally offset second holes of adjacent rows also mean that several expander holders can be attached to the second perforated plate in a space-saving manner but at a sufficient distance from one another.

According to a preferred embodiment, the lower side of the catching base expander holder can be firmly bonded or bondable, in particular welded or weldable, to an axial side of the second perforated plate facing the first perforated plate. In this way, the expander holder can be easily placed/ put axially from above (in the insertion direction of the tool to be inserted) on/onto the retaining device and firmly bonded thereto. Alternatively or additionally, the upper side of the catching base can be firmly bonded or bondable, in particular welded or weldable, to an axial side of the second perforated plate applied to the first perforated plate. In this way, the expander holder can be easily placed/put/plugged axially from below (against the insertion direction of the tool to be inserted) onto/on the retaining device and firmly bonded thereto.

According to the preferred embodiment, the expander holder, with its clamping arms passing/reaching through the second holes, can be placed on one of the junction points against the insertion direction of the tool to be inserted in such a way that the catching base projects axially from the second perforated plate as an axial spacer. In other words, the second perforated plate can thereby be kept spaced apart from, for example, a receiving box into which the second perforated plate is inserted in the insertion direction of the tool. This means that a lower side of the second perforated plate can be kept axially spaced from the receiving box by the thickness of the catching base, so that flushing with cleaning fluid is improved.

According to a preferred embodiment, the first holes of the first perforated plate can be arranged in parallel spaced rows and the hole centers of two adjacent rows can be arranged offset from each other by one crosspiece width of the second crosspieces. This ensures alignment of the first holes with the junction points and thus with the expander holders. In this way, several expander holders (and thus several tools) can be attached to the retaining device in a space-saving manner but with sufficient spacing from one another.

In other words, the disclosure relates to a welded-on clamping spring, in which a metal clamp elastically, i.e. resiliently, supporting a tool to be inserted can be attached by means of firmly bonded, in particular (spot) welding, fastening below (from below) or above (from above) to a second perforated plate of a retaining device, which is spaced apart from a first perforated plate of a retaining device having first holes for inserting the tool. A shape of the first holes can stabilize the position of the tool and/or limit the tool shank diameters by different inner diameters. A shape of second holes of the second perforated plate and/or a distance of the second perforated plate can limit an insertion depth of the tools.

BRIEF DESCRIPTION OF THE DRAWINGS

FIGS. 1 to 23 show various views and modifications of a positively/form and non-positively/force-fitting attachable expander holder and a tool set comprising the expander holder according to an aspect of the disclosure.

DETAILED DESCRIPTION

Embodiments of the present disclosure are described below based on the accompanying Figures.

Figure 8:
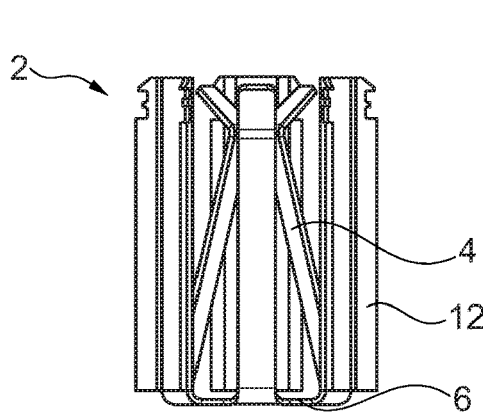
Figure 9:
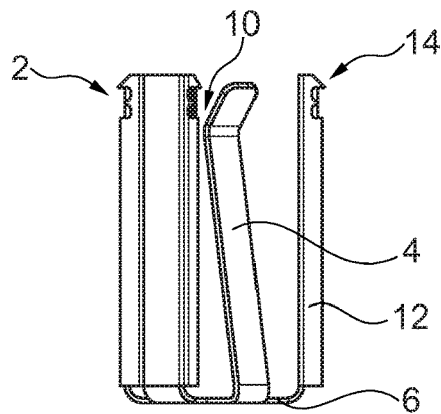
Figure 10:
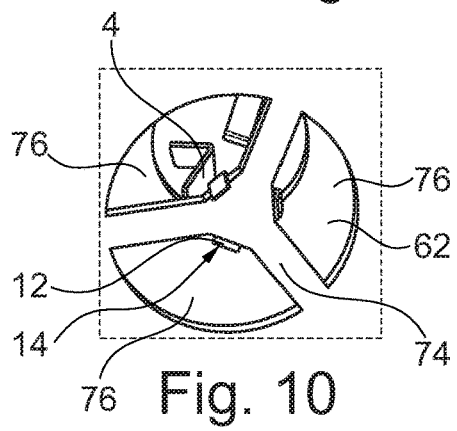
Figure 11:
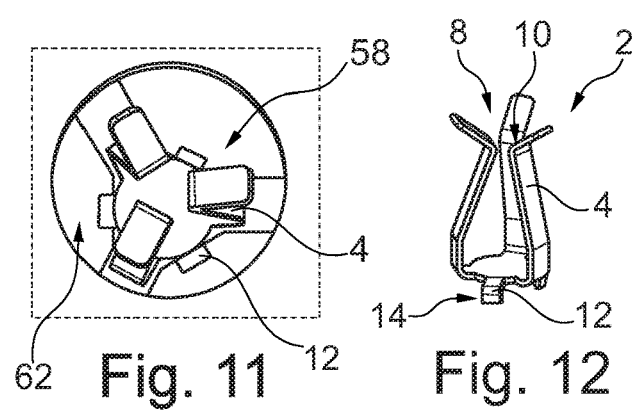
Figure 12:
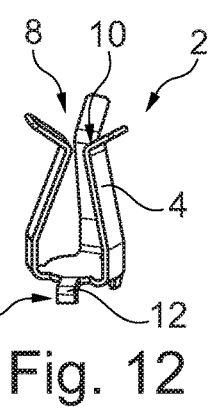
Figure 13:
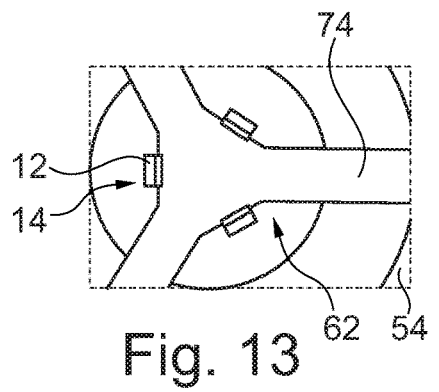
Figure 14:
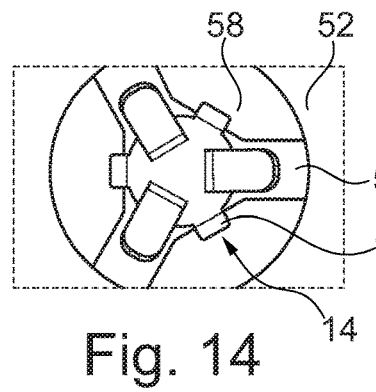
Figure 15:
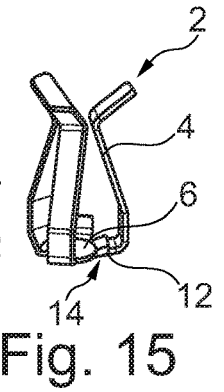
Figure 16:
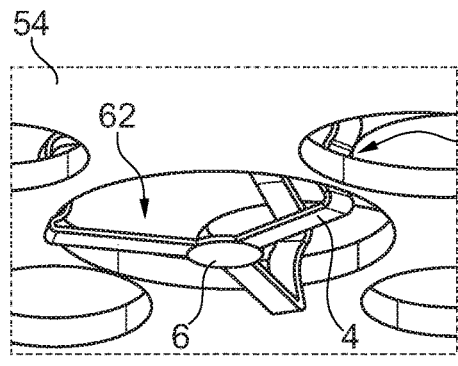
Figure 17:
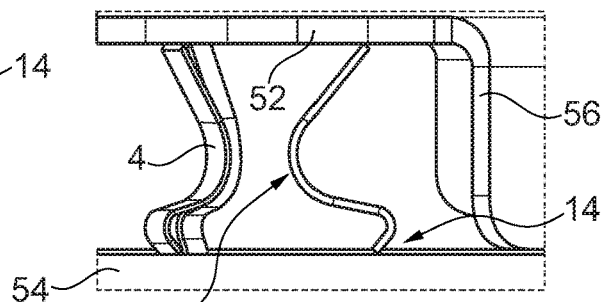
Figure 18:
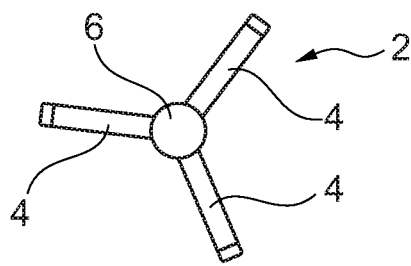
Figure 19:
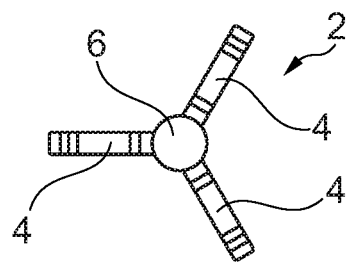
Figure 20:
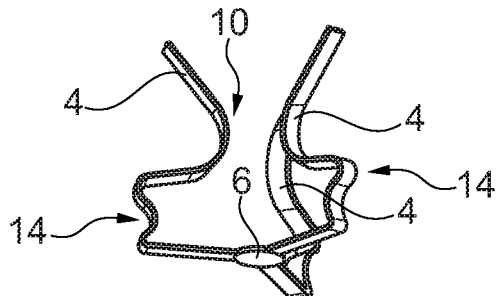
Figure 21:
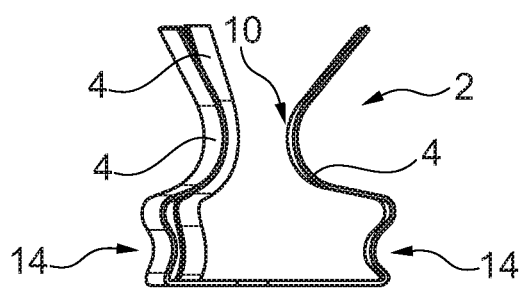
Figure 22:
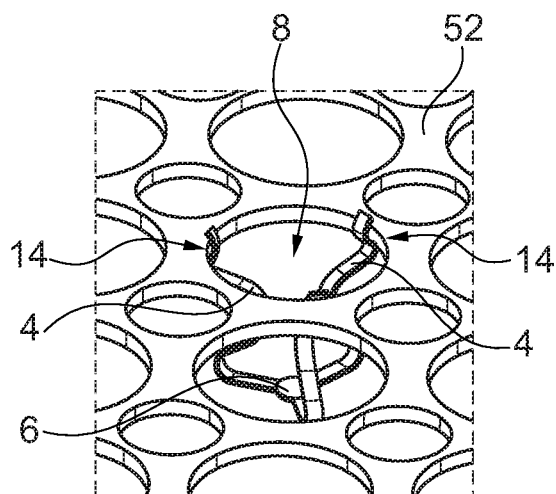
Figure 23:
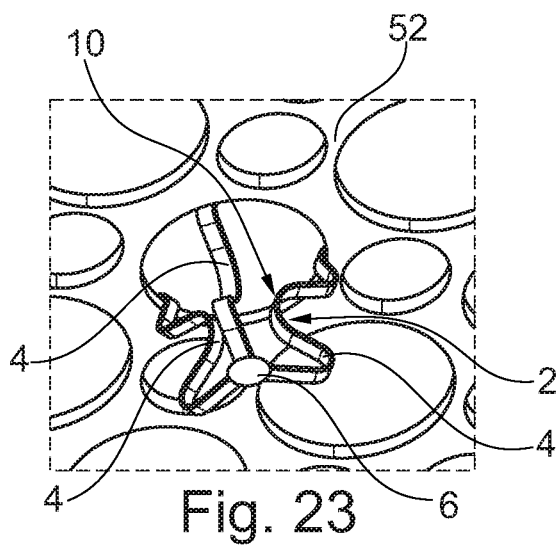

FIGS. 1 to 23 show a first embodiment of the present disclosure in various modifications. FIGS. 1 to 9 show a first modification of the first embodiment. FIGS. 10 to 12 show a second modification of the first embodiment. FIGS. 13 to 15 show a third modification of the first embodiment. FIGS. 16 to 21 show a fourth modification of the first embodiment. FIGS. 22 and 23 show a fifth modification of the first embodiment.

FIGS. 1 to 5 show an expander holder 2 of a tool set 100 inserted or plugged into a retaining device 50 of the tool set 100. FIGS. 6 to 9 show a representation of the expander holder 2 that is not plugged or inserted into the retaining device 50 of the tool set 100.

The expander holder 2 has a number of circumferentially spaced clamping arms 4 and a preferably flat catching base 6 from which the clamping arms 4 extend in the axial direction, i.e. perpendicular to the catching base 6. Alternatively, the catching base 6 may be curved or have an embossing, protrusion or the like, although this is not shown. In the embodiment shown, the expander holder 2 has three clamping arms 4. Alternatively, the expander holder 2 could have more than 3, for example 4, 5 or 6 clamping arms 4. The clamping arms 4 are elastically deformable and form an insertion opening 8 at an open front side of the expander holder 2 for inserting a tool (not shown). The clamping arms 4 can be arranged evenly distributed over the circumference of the expander holder 2. Preferably, the clamping arms 4 are bending elastic and made of a metal, for example a spring steel such as the material 1.4310. The clamping arms 4 preferably form a funnel at their free end portions, which narrows in the insertion direction of the tool to be held.

The clamping arms 4 have radially inwardly projecting engagement portions 10 for force-fitting and/or form-fitting contacting of the tool in order to hold the tool. When the tool is inserted (and the engagement portions 10 are contacted), the clamping arms 4 are resiliently pressed outwards in the radial direction of the expander holder 2. The resulting elastic tension of the clamping arms 4 holds/clamps the inserted tool between the clamping arms 4. This means that an outer diameter of a receiving space formed radially inside the expander holder 2 for receiving the tool is limited radially outward by the engagement portions 10 or the elastic deformability of the clamping arms 4. The engagement portions 10 are preferably designed in such a way that the contact surface between the clamping arms 4 and the received tool is as small as possible (linear and/or punctiform). Since the surface of the tool forms a contact site with the expander holder 2 only at the points/lines defined by the engagement portions 10, cleaning fluid can flow around the tool over a large area.

The expander holder 2 has the catching base 6, which is formed on the end portion of the expander holder 2 opposite the insertion opening 8. The catching base 6 extends substantially in the form of a plate perpendicular to the axial direction of the expander holder 2. Alternatively, the catching base can also be embossed. In the embodiment shown, the catching base 6 has the shape of a circle. Alternatively, the catching base 6 could, for example, be annular, oval or substantially triangular in shape. The catching base 6 could also be provided with one or more holes, or with a central substantially frustoconical recess into which an end of a tool can be self-centeringly received. The frustoconical surface of this recess can thereby also be of a slotted or interrupted design, and the "tip" of the frustoconical surface can be of an open or closed design. The clamping arms 4 extend from the radial outer edge of the catching base 6 in the axial direction towards the open front side of the expander holder 2. Preferably, the catching base 6 is made of a metal, for example a spring steel, such as the material 1.4310. For example, the clamping arms 4 may be attached to the catching base 6 via an acute angle corner connector/corner connection region/bending site, so that the angle of inclination at the corner connector between the clamping arms 4 and the catching base 6 is increased by the insertion of the tool against the elasticity of the clamping arms 4. In particular, the catching base 6 can be integrally/materially connected to the clamping arms 4.

Figure 27:
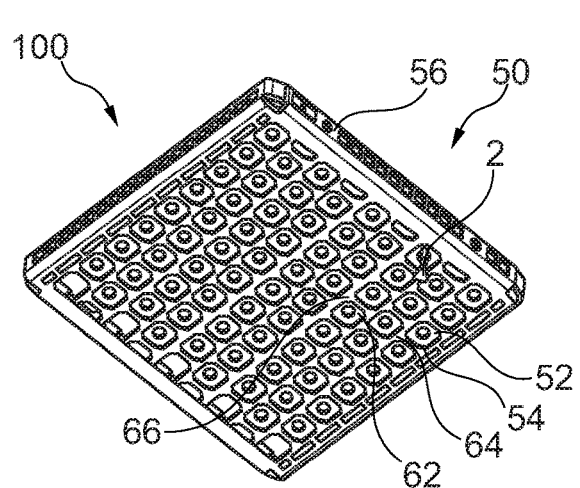
FIGS. 27 to 38 show various views and modifications of a firmly bonded expander holder and a tool set comprising the expander holder according to another aspect of the disclosure.
Figure 28:
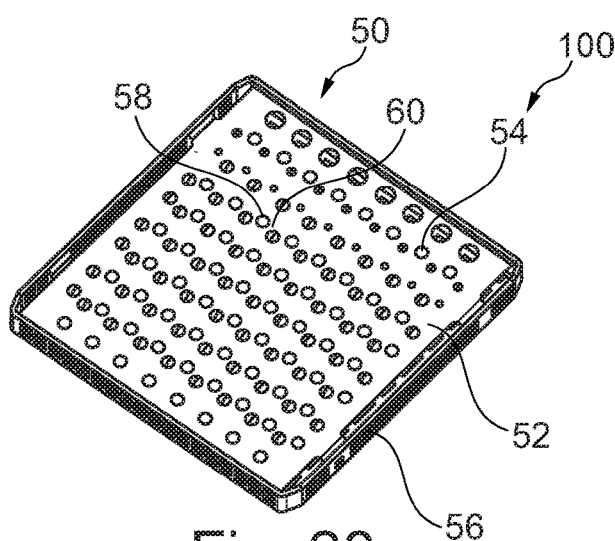
Figure 29:
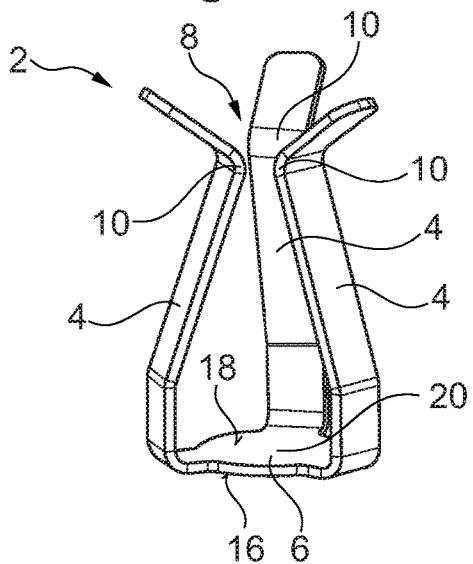
Figure 30:
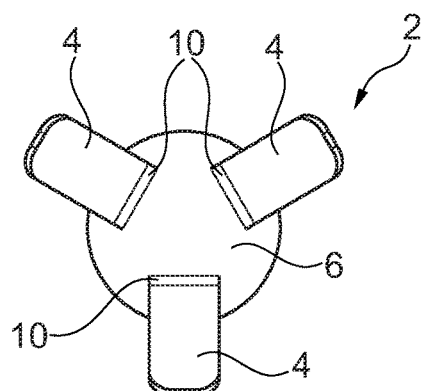
Figure 31:
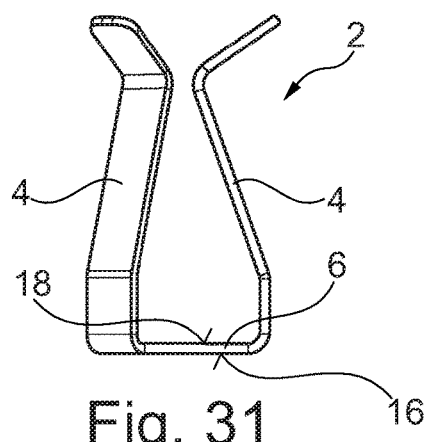
Figure 32:
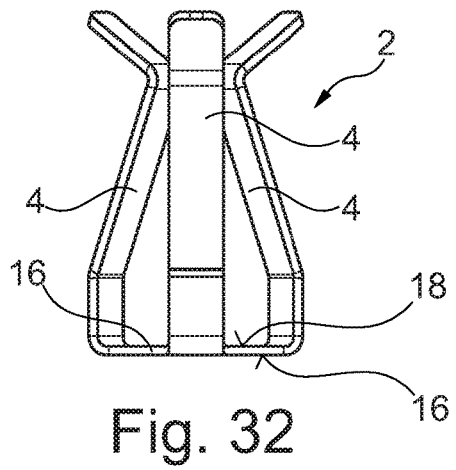

The expander holder 2 can be inserted into the retaining device 50 of the tool set 100. In particular, the expander holder 2 can be attached directly to the retaining device 50. The retaining device 50 has a first perforated plate (perforated matrix/sleeve sheet/screen structure) 52 and a second perforated plate (grid plate/perforated matrix/bottom plate/screen structure) 54. The two perforated plates 52, 54 are arranged parallel to each other and are connected to each other, for example, via outer walls (a frame) 56 (cf. FIG. 17 or FIGS. 27 and 28) or crosspieces.

The first perforated plate 52 has a number of first holes (recesses/perforations) 58. In the illustrated embodiment, the first holes 58 are substantially round in shape and may have different diameters to accommodate different tool shank diameters. Alternatively, the first holes 58 may have a substantially rectangular or square shape or be star-shaped, although this is not shown. The first holes 58 are separated from each other by material of the first perforated plate 52, for example by first crosspieces 60. For example, the first holes 58 may be arranged in straight rows, as shown in FIG. 1. That is, the hole centers of the first holes 58 of adjacent rows and/or the hole centers of adjacent first holes 58 of a row each have the same spacing, i.e., have the same hole pitch. In FIG. 1, the expander holder 2 is inserted into one of the first holes 58 in insertion direction of the tool, so that it dips into the first perforated plate 52 in insertion direction of the tool, i.e. in direction towards the second perforated plate 54.

The second perforated plate 54 has a number of second holes (recesses/perforations) 62. The second holes 62 are substantially square (cf. FIG. 2) or substantially round (cf. FIGS. 10, 13 and 16). The second holes 62 are separated from each other by material of the second perforated plate 54, for example by second crosspieces 64. Preferably when square in shape, the second holes 62 may be arranged in straight rows, for example. That is, the hole centers of the second holes 62 of adjacent rows and/or the hole centers of adjacent second holes 62 of a row each have the same spacing, that is, have the same hole pitch. That is, the second crosspieces 64 are arranged rectilinearly as well as parallel and/or perpendicular to each other. The second crosspieces 64 intersect at their junction points 66.

The first holes 58 and the second holes 62 can be arranged in alignment with each other in the axial direction. Alternatively, the second holes 62 can also be arranged not in alignment with the first holes 58 in the axial direction, with the junction points 66 preferably being arranged in alignment with the first holes 58 in the axial direction in the case of a non-aligned arrangement.

In an advantageous further development (cf. FIGS. 3 and 4), at least one of the first holes 58 can have radially inwardly projecting separation crosspieces 68 formed by material of the first perforated plate 52. The separation crosspieces 68 serve as form-fitting anti-turn devices for the expander holder 2. Preferably, the at least one hole of the first holes 58 (per fastening portion 14 described in detail later) has at least two radially inwardly projecting separation crosspieces 68, each forming a stop in a circumferential direction of the expander holder 2. That is, each of the fastening portions 14 is arranged between two separation crosspieces 68 in the circumferential direction of the expander holder 2. The separation crosspieces 68 divide the at least one hole of the first holes 58 into a plurality of hole portions separated from each other. Preferably, the separation crosspieces 68 can be formed in such a way, in particular (approximately two separation crosspieces 68 in each case) can be connected to each other in such a way that they form, in particular together with the outer diameter of the hole, several substantially triangular or circular sector-shaped fastening portion perforations 70, through each of which a fastening portion 14 can be passed (axially, preferably against the insertion direction). In addition or alternatively, the separation crosspieces 68 can be formed in such a way, in particular (approximately two separation crosspieces 68 in each case) can be connected to one another in such a way that they form, in particular together with the outer diameter of the hole, a star-shaped clamping arm perforation 72. The clamping arm perforation 72 preferably has avoidance gaps extending radially outwards from the hole center in a star shape, the width of which is greater than a width of the clamping arms 4. This allows the clamping arms 4 to be elastically displaced in the radial direction within the clamping arm perforation 72, preferably guided by the separation crosspieces 68. Preferably, the clamping arm perforation 72 has at least as many avoidance gaps as the expander holder 2 has clamping arms 4.

In an advantageous further embodiment (see FIGS. 10 and 11 or FIGS. 13 and 14), the second holes 62 may have radially inwardly projecting separation crosspieces 74 formed by material of the second perforated plate 54. Preferably, at least one hole of the second holes 62 has the radially inwardly projecting separation crosspieces 74 that divide the subdivided second hole 62 into a plurality of hole portions 76. Preferably, the separation crosspieces 74 may intersect at a center point of the subdivided second hole 62. The hole portions 76 preferably have the same shape and may, for example, be substantially triangular or shaped like a sector of a circle. That is, the separation crosspieces 74 may be formed, in particular connected to each other, such that they intersect at the hole center and extend radially outwardly from the hole center in a star shape, thereby forming, in particular together with the outer diameter of the hole, the plurality of substantially triangular or circular sector-shaped hole portions 76.

The expander holder 2 has a plurality of fastening portions 14 formed, for example, on fastening arms 12 (cf. FIGS. 1 to 15), which are used for force-fitting and form-fitting the expander holder 2 to the retaining device 50 of the tool set. In the illustrated embodiment, the expander holder 2 has three circumferentially spaced fastening arms 12. Alternatively, the expander holder 2 could have more than three fastening arms 12. The fastening arms 12 may be equally distributed around the circumference of the expander holder 2. Preferably, the number of fastening arms 12 corresponds to the number of clamping arms 4. In particular, the fastening arms 12 may be arranged alternately with the clamping arms 4 in the circumferential direction of the expander holder 2. Preferably, the fastening arms 12 are made of a metal, for example a spring steel, such as the material 1.4310. For example, the fastening arms 12 may be fixedly attached to the catching base 6, in particular via a corner connector/corner connection region/bending site. In particular, the fastening arms 12 can be integrally/materially connected to the catching base 6 and/or to the clamping arms 4.

In particular, the fastening portion 14 serve for direct positive/form-fitting and non-positive/force-fitting fastening to the retaining device 50 of the tool set 100, in particular to the first perforated plate 52 and/or the second perforated plate 54. The fastening portions 14 are adapted and provided to cooperate directly with the first perforated plate 52 or the second perforated plate 54 for fastening to this perforated plate 52 and to embrace/grip around this perforated plate 52, 54 in a radially clamping manner axially in such a way that they engage behind the perforated plate material in the thickness direction of the perforated plate in a form-fitting manner against an insertion direction of the tool to be inserted.

The catching base 6 of the expander holder 2 is formed by a flat plate. Alternatively, the catching base 6 may be curved, for example substantially frustoconical in shape, or have an embossing, protrusion or the like, although this is not shown. A lower side 16 of the catching base 6 is an axial side of the catching base 6 facing away from the clamping arms 4, i.e. an axial outer surface of the expander holder 2. An upper side 18 of the catching base 6 is an axial side of the catching base 6 facing towards the clamping arms 4, i.e. an axial inner surface (arranged between the clamping arms 4) of the expander holder 2. The upper side 18 of the catching base 6 formed an axial stop surface for the tool to be inserted.

In the first modification shown in FIGS. 1 to 9, the fastening arms 12 extend from the catching base 6 in the axial direction and form the fastening portions 14 at their free, radially outwardly bent end portions, for example in the form of radially outwardly oriented latching lugs. In this case, the fastening arms 12 extend from the catching base 6 in the same direction as the clamping arms 4. The fastening arms 12 shown in FIGS. 1 to 9 extend essentially as far in the axial direction as the clamping arms 4. In particular, an axial extent of the fastening arms 12 shown in FIGS. 1 to 9 corresponds essentially to a distance between the first perforated plate 52 and the second perforated plate 54. The radially outwardly bent or protruding end portions forming the fastening portions 14 are adapted and provided to pass through one of the first holes 58 so as to clampingly engage from radially inside/inwardly behind the perforated plate material of the first perforated plate 52 in thickness direction of the perforated plate. In other words, the fastening portions 14 clasp the first perforated plate 52 from below.

In the second modification shown in FIGS. 10 to 12, the fastening arms 12 extend from the catching base 6 in the axial direction and form the fastening portions 14, for example in the form of fixing claws, at their free, radially inwardly bent end portions. The fastening arms 12 extend from the catching base 6 in an opposite direction to the clamping arms 4. The fastening arms 12 shown in FIGS. 10 to 12 are (substantially) shorter in the axial direction than the clamping arms 4. In particular, an axial extension of the fastening arms 12 shown in FIGS. 10 to 12 substantially corresponds to the thickness of the second perforated plate 54. The radially inwardly bent or protruding end portions forming the fastening portions 14 are adapted and provided to pass through one of the second holes 62 (or hole portions 74 thereof, respectively) so as to clampingly engage behind the perforated plate material of the second perforated plate 54 from radially outside/outwardly in the thickness direction of the perforated plate. The catching base 6 rests with its lower side 16 axially on perforated plate material of the second perforated plate 54. In other words, the fastening portions 14 clasp the second perforated plate 54 from above.

In the third modification shown in FIGS. 13 to 15, the fastening arms 12 extend from the catching base 6 in the axial direction and form the fastening portions 14, for example in the form of fixing claws, at their free, radially inwardly bent end portions. The fastening arms 12 extend from the catching base 6 in the same direction as the clamping arms 4. The fastening arms 12 shown in FIGS. 13 to 15 are (substantially) shorter in the axial direction than the clamping arms 4. In particular, an axial extension of the fastening arms 12 shown in FIGS. 13 to 15 substantially corresponds to the thickness of the second perforated plate 54. The radially inwardly bent or protruding end portions forming the fastening portions 14 are adapted and provided to pass through one of the second holes 62 (or hole portions 74 thereof) so as to clampingly engage from radially outside/outwardly behind the perforated plate material of the second perforated plate 54 in the thickness direction of the perforated plate. The catching base 6 axially abuts the perforated plate material of the second perforated plate 54 with its upper side 16. In other words, the fastening portions 14 clasp the second perforated plate 54 from below.

In the fourth modification shown in FIGS. 16 to 21, the clamping arms 4 form the engagement portions 10 at a first axial portion and the fastening portions 14, for example in the form of curved sections, at a second axial portion immediately adjacent thereto in the axial direction. The second axial portion is located radially outside the first axial portion. The second axial portion is formed between the catching base and the first axial portion of the clamping arm 4. The second axial portion is a radially inwardly bent, approximately U-shaped portion, of the clamping arm 4 and is adapted and provided to pass through one of the second holes 62 of the second perforated plate 54 so that it clamps from radially inside/inwardly to engage behind or around the perforated plate material in thickness direction of the perforated plate. The U-shaped portion may preferably have an opening oriented radially outwardly. In the assembled state, the catching base 6 of the expander holder 2 is preferably located below the second perforated plate 54 (i.e. outside the space between the first perforated plate 52 and the second perforated plate 54).

In the fifth modification shown in FIGS. 22 and 23, the clamping arms 4 form the engagement portions 10 at a first axial portion and the fastening portions 14 at a second axial portion immediately adjacent thereto in the axial direction. The second axial portion is located radially outside the first axial portion. The second axial portion is formed at a free end portion of the clamping arm 4. The second axial portion is a radially inwardly bent, approximately U-shaped portion of the clamping arm 4 and is adapted and provided to pass through one of the first holes 58 of the first perforated plate 52 so that it clamps from radially inside/inwardly to engage behind or around the perforated plate material in the thickness direction of the perforated plate. The U-shaped portion may preferably have a radially outwardly oriented opening. The fifth mode shown in FIGS. 22 to 23 may be attached to a retaining device 50 in the form of a single perforated plate.

Figure 24:
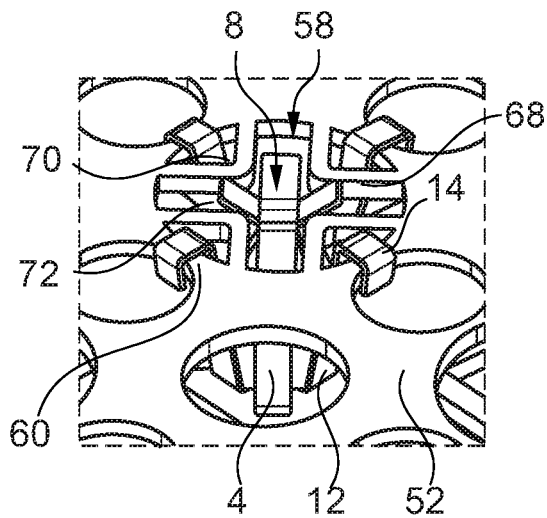
FIGS. 24 to 26 show various views and modifications of a form-fitting hookable expander holder and a tool set comprising the expander holder according to another aspect of the disclosure.
Figure 25:
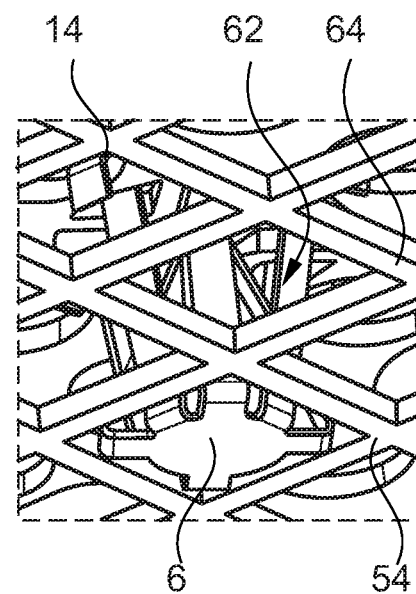
Figure 26:
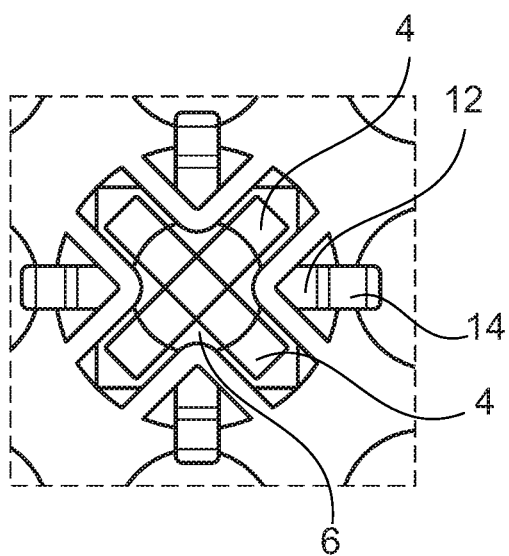

FIGS. 24 to 26 show a second embodiment of the present disclosure. The expander holder 2 of the second embodiment suspended in the retaining device 50 is shown in FIG. 24 in a perspective view from above, in FIG. 25 in a perspective view from below, and in FIG. 26 in a top view.

The expander holder 2 has several, in the illustrated embodiment four, circumferentially spaced clamping arms 4. Alternatively, the expander holder 2 could also have, for example, three clamping arms 4 or more than four clamping arms 4. The clamping arms 4 may be equally distributed around the circumference of the expander holder 2. The clamping arms 4 are elastically deformable and form the insertion opening 8 for inserting the tool (not shown) at the open front side of the expander holder 2. Preferably, the clamping arms 4 are bending elastic and made of a metal, for example a spring steel, such as material 1.4310. The clamping arms 4 preferably form a funnel at their (frontal) free end portions, which narrows in the insertion direction of the tool to be held.

The clamping arms 4 have radially inwardly projecting engagement portions 10 for force-fitting and/or form-fitting contacting of the tool in order to hold the tool. By inserting the tool (and contacting the engagement portion 10), the clamping arms 4 are resiliently pressed outward in the radial direction. The resulting elastic tension of the clamping arms 4 holds/clamps the inserted tool between the clamping arms 4. This means that an outer diameter of a receiving space formed radially inside the expander holder 2 for receiving the tool is limited radially outward by the engagement portions 10 or the elastic deformability of the clamping arms 4. The engagement portions 10 are preferably designed in such a way that the contact surface between the clamping arms 4 and the received tool is as small as possible (linear and/or punctiform). Since the surface of the tool forms a contact site with the expander holder 2 only at the points/lines defined by the engagement portions 10, cleaning fluid can flow around the tool over a large area.

The expander holder 2 has the catching base 6, which is formed at the end portion of the expander holder 2 opposite the insertion opening 8. The catching base 6 can serve as an axial stop and prevent the tool from being inserted too deeply. The catching base 6 extends substantially plate-shaped perpendicular to the axial direction of the expander holder 2. In the illustrated embodiment, the catching base 6 has the shape of a circle. Alternatively, the catching base 6 could, for example, be annular, oval or substantially triangular in shape. The catching base 6 may be flat or curved, for example substantially frustoconical in shape. From the catching base 6, the clamping arms 4 extend in axial direction towards the insertion opening 8. The clamping arms 4 extend from the radial outer edge of the catching base 6. Preferably, the catching base 6 is made of a metal, for example a spring steel, such as the material 1.4310. For example, the clamping arms 4 may be attached to the catching base 6 via an acute-angled corner connector/acute-angular corner connection region/bending site, such that the angle of inclination at the corner connector between the clamping arms 4 and the catching base 6 is increased by the insertion of the tool against the elasticity of the clamping arms 4. In particular, the catching base 6 can be integrally/materially connected to the clamping arms 4.

The expander holder 2 has a plurality of fastening arms 12 that serve to fasten the expander holder 2 to the retaining device 50 of the tool set. In the illustrated embodiment, the expander holder 2 has four circumferentially spaced fastening arms 12. Alternatively, the expander holder 2 could have, for example, three fastening arms 12 or more than four fastening arms 12. The fastening arms 12 may be equally distributed around the circumference of the expander holder 2. Preferably, the number of fastening arms 12 corresponds to the number of clamping arms 4. In particular, the fastening arms 12 may be arranged alternately with the clamping arms 4 in circumferential direction. Preferably, the fastening arms 12 are made of a metal, for example a spring steel, such as the material 1.4310. For example, the fastening arms 12 may be fixedly attached to the catching base 6, in particular via a corner connector/corner connection region/bending site. In particular, the fastening arms 12 may be integrally/materially connected to the catching base 6 and/or to the clamping arms 4. The fastening arms 12 extend from the catching base 6 in axial direction towards the insertion opening 8. The fastening arms 12 extend from the radial outer edge of the catching base 6. Preferably, the expander holder 2 is designed as a metallic bending forming part.

The fastening arms 12 each have a hook-like fastening portion 14 on their end portions arranged on the open front side of the expander holder 2 for hooking onto the retaining device 50. The fastening portion 14 is bent or angled in such a way that it can be hooked onto the retaining device 50 (in the insertion direction of the tool). Preferably, the fastening portion 14 can be designed and provided in such a way that it engages radially and axially behind the retaining device 50. In other words, the fastening portion 14 embraces/grips around the retaining device 50 axially and radially, in particular for fixing the radial position and the axial position of the expander holder 2 on the retaining device 50.

In particular, the fastening portion 14 may form a U-shaped profile. In the illustrated embodiment, a base portion forming a base of the U-shaped profile extends substantially in the radial direction (i.e., perpendicular to the axial direction). The base portion thus lies flat against the retaining device 50. Legs of the U-shaped profile extend from the ends of the base portion substantially in the axial direction in the same direction. A radially inner leg of the two legs can extend longer in the axial direction, preferably up to the catching base 6, than a radially outer leg of the two legs. That is, the profile of the fastening portion 14 has an insertion opening that can preferably be oriented radially outward and/or preferably axially toward the catching base 6, i.e., opposite the insertion direction of the tool. Through the radially outwardly oriented insertion opening of the U-profile, the fastening portion 14 can be attached to the retaining device 50 from radially inside. Through the insertion opening of the U-profile, which is aligned axially against to the insertion direction of the tool, the fastening portion 14 can be attached to the retaining device 50 in the insertion direction of the tool.

The catching base 6 of the expander holder 2 is formed by a flat plate, for example. Alternatively, the catching base 6 may be curved, for example substantially frustoconical, or have an embossing, protrusion or the like, although this is not shown. The lower side 16 of the catching base 6 is the axial side of the catching base 6 facing away from the clamping arms 4, i.e. an axial outer surface of the expander holder 2. The upper side 18 of the catching base 6 is the axial side of the catching base 6 facing towards the clamping arms 4, i.e. an axial inner surface (arranged between the clamping arms 4) of the expander holder 2. The upper side 18 of the catching base 6 forms an axial stop surface for the tool to be inserted.

The retaining device 50 of the second embodiment comprises the first perforated plate 52. The first perforated plate 52 has a number of first holes (recesses/perforations) 58, which in the illustrated embodiment are round in shape and have different diameters to accommodate different tool shank diameters. Alternatively, the first holes 58 may have a substantially rectangular or square shape or be star-shaped, although this is not shown. The first holes 58 are separated from each other by first crosspieces 60. For example, as shown in FIG. 24, the first holes 58 may be arranged in rows offset by 60°. That is, the hole centers of adjacent rows are arranged centrally offset from each other. The retaining device 50 may include the second perforated plate 54 arranged in spaced parallel relation to the first perforated plate 52 and connected to the first perforated plate 52, for example, via the frame not shown in FIGS. 24 to 26. The second perforated plate 54 has a number of second holes (recesses/perforations) 62, which may have a square shape. For example, the holes 62 may be arranged in straight rows as shown in FIG. 25. The holes 62 may be separated from each other by rectilinear crosspieces 64. The second perforated plate 54 may serve as an anti-turn device for the expander holder 2. The second embodiment shown in FIGS. 24 to 26 may also be attached to a retaining device 50 formed as a single plate/single perforated plate having only the first perforated plate 52.

The expander holder 2 of the second embodiment is attached to the first perforated plate ix) 52 of the retaining device 50. In particular, the expander holder 2 is inserted into one of the first holes 58. The hook-like fastening portion 14 axially and radially engages behind the crosspiece 60 so that it, in particular the radially outer leg of the U-shaped profile, form-fits into an adjacent first hole 58. In other words, the fastening portion 14 passes through the first hole 58 into which the expander holder 2 is inserted, angled radially outwardly so that it extends outwardly parallel/entirely along the perforated plate material and axially engages behind the crosspiece 60 bounding the first hole 58, and is angled axially toward the catching base 6 so that it form-fits into the adjacent first hole 58 and radially engages behind the crosspiece 60 bounding the first hole 58. Thus, the fastening portion 14 embraces/grips around the perforated plate material in the axial direction, in particular against the insertion direction of the tool. That is, the fastening portion 14 is hooked onto the crosspieces 60 of the first perforated plate 52.

In an advantageous further development, at least one of the first holes 58 can have the separation crosspieces 68 projecting radially inwards and formed by material of the first perforated plate 52. The separation crosspieces 68 form a form-fitting anti-turn device for the expander holder 2, in particular for the fastening portions 14. Preferably, the at least one hole of the first holes 58 (per fastening portion 14) has at least two radially inwardly projecting separation crosspieces 68, which each form a stop in a circumferential direction of the expander holder 2. That is, each of the fastening portions 14 is arranged between two separation crosspieces 68 in the circumferential direction of the expander holder 2.

The separation crosspieces 68 divide the at least one hole of the first holes 58 into several hole portions separated from each other. Preferably, the separation crosspieces 68 can be formed, in particular (about two separation crosspieces 68 each) can be connected to each other in such a way that they form, in particular together with the outer diameter of the hole, several substantially triangular or circular sector-shaped fastening portion perforations 70. Each fastening portion perforation 70 is adapted to the fastening portion 14, in particular the base portion of the U-profile, in such a way that the fastening portion 14 can be passed axially through the fastening portion perforation 70 (preferably against the insertion direction). In addition or alternatively, the separation crosspieces 68 can be formed, in particular (approximately two separation crosspieces 68 in each case) can be connected to one another in such a way that they form, in particular together with the outer diameter of the hole, a star-shaped clamping arm perforation 72. The clamping arm perforation 72 preferably has avoidance gaps extending radially outwards in a star shape from the hole center, the width of which is greater than a width of the clamping arms 4. This allows the clamping arms 4 to be elastically displaced in the radial direction (limited) within the clamping arm perforation 72, preferably guided by the separation crosspieces 68. Preferably, the clamping arm perforation 72 has at least as many avoidance gaps as the expander holder 2 has clamping arms 4. In the embodiment shown in FIGS. 24 to 26, the clamping arm perforation 72 has a plus-shaped/cross-shaped cross-section. An inner diameter formed by the separation crosspieces 68 may limit the shank diameter of the tool to be inserted.

In FIGS. 27 to 38, a third embodiment is shown. The retaining device 50 of the third embodiment is shown in perspective from below in FIG. 27 and in perspective from above in FIG. 28. The first perforated plate (perforated matrix/sleeve sheet/screen structure) 52 and the second perforated plate (grid plate/perforated matrix/bottom plate/screen structure) 54 are arranged parallel to each other and are connected to each other via the outer walls (frame) 56.

The first perforated plate 52 has a number of first holes (recesses/perforations) 58, which in the illustrated embodiment are round in shape and have different diameters to accommodate different tool shank diameters. Alternatively, the first holes 58 could have a substantially rectangular or square shape or be star-shaped, although this is not shown. Alternatively, the first holes 58 could be formed with the same diameter. An expander holder 2 is pluggable/insertable or inserted/inserted into each of the first holes 58. The first holes 58 are separated from each other by first crosspieces 60.

The second perforated plate 54 has a number of second holes (recesses/perforations) 62 that are substantially square, preferably substantially rectangular or square, in shape and are separated from each other by the second crosspieces 64. In the illustrated embodiment, each of the second holes 62 has the same shape. Alternatively, the second holes 62 could have different sizes.

The second crosspieces 62 extend rectilinearly and parallel to the outer edges of the second perforated plate 54. The second crosspieces 62 form a lattice structure and intersect each other substantially at right angles at their junction points 66. The second holes 62 are arranged in rows and the second holes 62 of directly adjacent rows are offset from each other, preferably centrally. Thus, the second holes 62 are arranged in 60°-offset rows. This means that the second crosspieces 64 form a T-junction at their junction points 66, or that each junction point 66 forms the edge of three adjacent second holes 62, in particular two corner points and one side edge. At the junction points 66, the second crosspieces 64 widen convexly outwardly at the corner points of the second holes 62, i.e., they curve convexly toward the hole center. This results in the second holes 62 having a substantially square shape, the corners of which are concavely curved inwardly (the corner points of which curve inwardly in an approximately quarter-circle shape). In other words, the second crosspieces 64 are widened in such a way that at their junction points 66 a circular area whose radius corresponds substantially to the width of the second crosspieces 64 can be arranged completely between the second holes 62. In other words, the second crosspieces 64 form a welding, soldering or gluing surface at the junction points 66 which is preferably substantially as large as an area of the catching base 6.

The first holes 58 are arranged in alignment with the junction points 66 of the second perforated plate 54, in particular with the center of the circular areas formed between the second holes 62, respectively. That is, the first holes 58 are arranged offset from (i.e., not aligned with) the second holes 60. In particular, the first holes 58 of the first perforated plate 52 may be arranged in parallel spaced rows and the hole centers of each two adjacent rows may be arranged offset from each other by a crosspiece width of the second crosspieces 64.

FIGS. 29 to 32 show different views of the expander holder 2 of the third embodiment. The expander holder 2 has elastically deformable clamping arms 4. The clamping arms 4 preferably form a funnel at their free end portions, which narrows in the insertion direction of the tool to be held. Insertion of the tool causes the diameter of the cavity bounded radially by the clamping arms 4 to expand radially, forming inclined contact surfaces for the tool to be inserted, and the clamping arms 4 are resiliently pressed outward in the radial direction. The resulting elastic tension of the clamping arms 4 clamps the inserted tool in the cavity between the clamping arms 4. The clamping arms 4 are preferably designed in such a way that the contact surface between the clamping arms and the inserted tool is as small as possible (linear and/or point-like). Since the surface of the tool forms a contact site with the expander holder 2 only at the points/lines defined by the engagement portions 10, the tool can be flushed by cleaning fluid over a large area.

The expander holder 2 has the catching base 6, which is formed at the end portion of the expander holder 2 opposite the insertion opening 8. The catching base 6 can serve as an axial stop and prevent the tool from being inserted too deeply. The catching base 6 extends substantially plate-shaped perpendicular to the axial direction of the expander holder 2. In the illustrated embodiment, the catching base 6 has the shape of a circle. Alternatively, the catching base 6 could, for example, be annular, oval or substantially triangular in shape. From the catching base 6, the clamping arms 4 extend in the axial direction towards the open front side. The clamping arms 4 extend from the radial outer edge of the catching base 6 in the axial direction. Preferably, the catching base 6 is made of a metal, for example a spring steel, such as the material 1.4310. For example, the clamping arms 4 may be attached to the catching base 6 via an acute-angled corner connector/angular corner connection region/bending site, so that the angle of inclination at the corner connector between the clamping arms 4 and the catching base 6 is increased by the insertion of the tool against the elasticity of the clamping arms 4. In particular, the catching base 6 can be integrally/materially connected to the clamping arms 4.

In the case of direct firmly bonded attachment of the expander holder 2 to the retaining device 50, the catching base 6 is formed by a flat, chamfer-free plate from which only the clamping arms 4 extend axially, i.e. in a direction perpendicular to the plate, and which forms a welding, soldering or gluing portion 20 in a central region on one or both of its flat sides. In other words, the expander holder 2 comprises the flat, chamfer-free catching base 6 from which the plurality of clamping arms 4, three in the illustrated embodiment, extend axially towards the open front side. Thus, only the clamping arms 4 extend from the radial outer edge of the catching base 6 in the axial direction.

The lower side 16 of the catching base 6 is the axial side of the catching base 6 facing away from the clamping arms 4, i.e. an axial outer surface of the expander holder 2. The upper side 18 of the catching base 6 is the axial side of the catching base 6 facing towards the clamping arms 4, i.e. an axial inner surface (arranged between the clamping arms 4) of the expander holder 2. The upper side 18 of the catching base 6 forms an axial stop surface for the tool to be inserted.

The lower side 16 and/or the upper side 18 of the catching base 6 have or form the preferably metallic welding, soldering or gluing portion 20, which is adapted and provided for the direct firmly bonded, in particular (spot) welding, attachment of the expander holder 2 to the retaining device 50, in particular the second perforated plate 54. If the welding, soldering or gluing portions 20 are formed on the lower side 16, the expander holder 2 can be placed axially from above (in the insertion direction of the tool to be inserted) on the retaining device 50 and firmly bonded thereto. If the welding, soldering or gluing portions 20 are formed on the upper side 18, the expander holder 2 can be placed axially from below (against the insertion direction of the tool to be inserted) on the retaining device 50 and firmly bonded thereto. In other words, the lower side 16 and/or the upper side 18 of the catching base 6 is welded or can be welded to the retaining device 50.

The expander holder 2 can be adapted and provided in such a way that it can be placed on the second perforated plate 54 of the retaining device 50 against an insertion direction of the tool to be inserted, so that the clamping arms 4 reach through the second holes 62 and the catching base 6 projects axially from the second perforated plate 54 as a spacer. In other words, the second perforated plate 54 can thereby be kept spaced apart from, for example, a (not shown) receiving box into which the second perforated plate 54 is inserted in the insertion direction of the tool. That is, a lower side of the second perforated plate 54 can be held axially spaced from the receiving box by the thickness of the catching base 6. According to one embodiment, the catching base 6 may comprise a weldable insert or a weldable coating.

FIGS. 33 to 38 show various views of the tool set 100 of the third embodiment, in which the expander holder 2 is attached to the retaining device 50. In one embodiment shown in FIGS. 33, 36 and 38, the upper side 18 of the catching base 6 is attached, preferably welded (by spot welding), to the retaining device 50, in particular to one of the junction points 66 of the second perforated plate 54. In a further development of the third embodiment shown in FIG. 34, the lower side 16 of the catching base 6 is attached to the retaining device 50, in particular to one of the junction points 66 of the second perforated plate 54, preferably welded (by spot welding).

Figure 34:
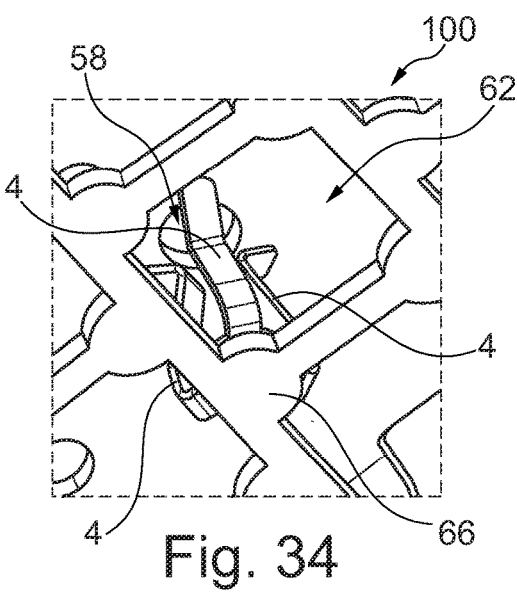
Figure 35:
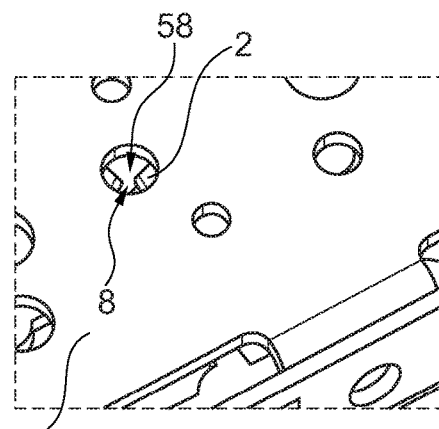

In the further development shown in FIG. 34, the expander holder 2 is placed on the second perforated plate 54 (from above, i.e. in the insertion direction of the mold). This means that the expander holder 2 can be arranged completely between the two perforated plates 52, 54. The catching base 6 and the circular surface formed by the junction point 66 are centered with respect to each other. The lower side/axial outer surface 16 of the expander holder 2 is attached to the axial side of the second perforated plate 54 facing the first perforated plate 52, in particular by spot welding.

Figure 33:
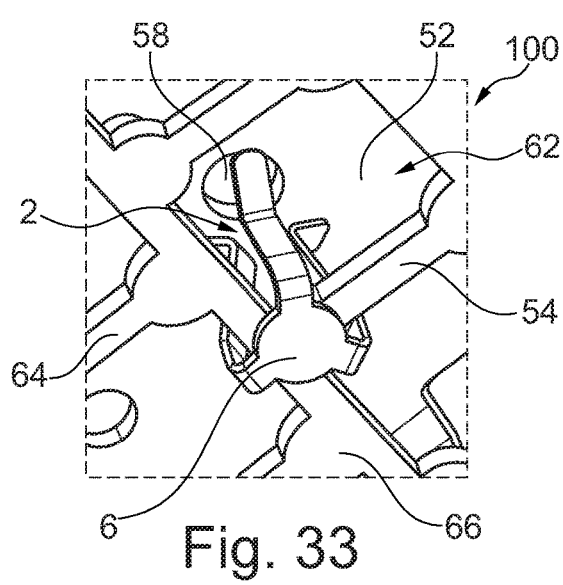
Figure 36:
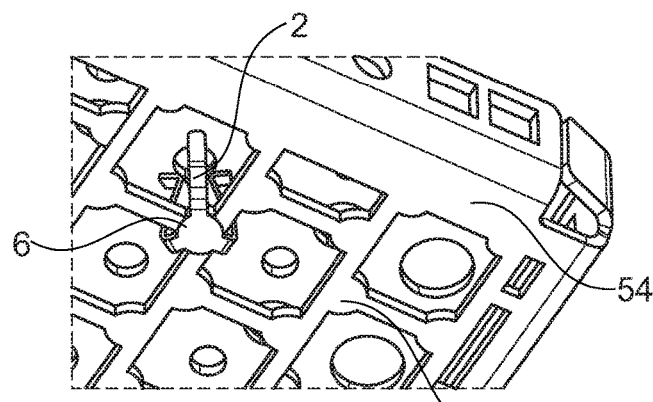
Figure 37:
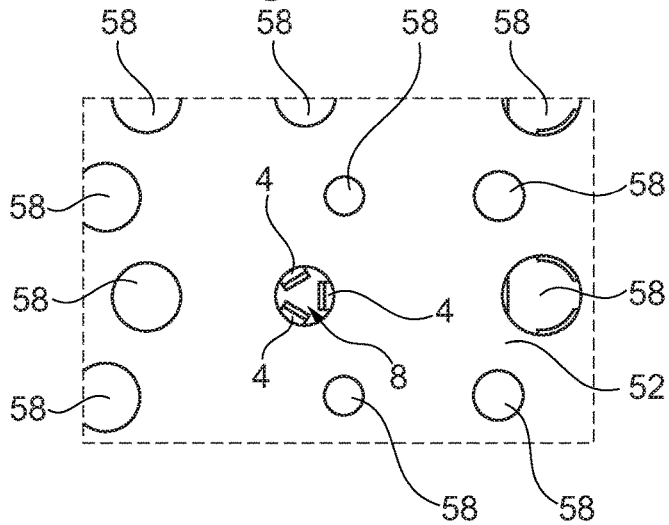
Figure 38:
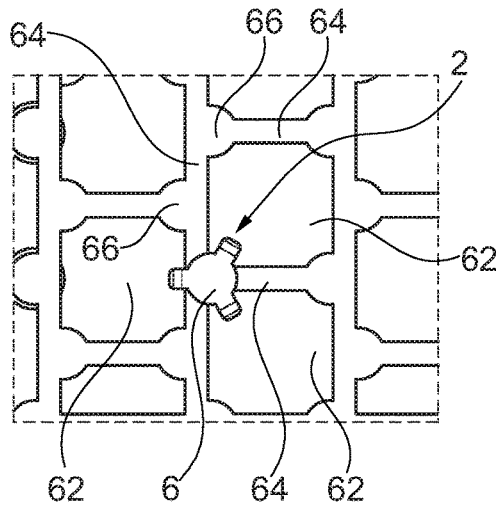

In the further development shown in FIGS. 33, 36 and 38, the expander holder 2 is mounted on or inserted into the second perforated plate 54 (from below, i.e. against the insertion direction of the tool). The catching base 6 and the circular surface formed by the junction point 66 are aligned centered to each other. The upper side/axial inner surface 18 of the expander holder 2 is attached to the axial side of the second perforated plate 54 facing away from the first perforated plate 52, in particular by spot welding. In other words, each of the clamping arms 4 axially penetrates/passes through one of the second holes 62. This means that the expander holder 2 protrudes axially on the axial side of the second perforated plate 54 facing away from the first perforated plate 52 by the thickness of the catching base 6. This has the advantage that the catching base 6 can serve as a spacer between the second perforated plate 54 and the (not shown) receiving box.

Due to the alignment of the first holes 58 with the junction points 66 of the second perforated plate, the insertion opening 8 formed by the clamping arms 4 is aligned with the first holes 58. Thus, the tool to be inserted can be inserted/plugged axially through the first perforated plate 52 in the insertion direction (up to the catching base 6 or the second perforated plate 54) and held radially by the engagement portions 10 of the expander holder 2.

The invention claimed is:

1. A tool set for plug-in holding of a surgical tool, the tool set comprising:
   A. an expander holder comprising:
      a plurality of clamping arms that are circumferentially spaced and elastically deformable, the clamping arms forming an insertion opening for insertion of the surgical tool on an open front side of the expander holder, the clamping arms having engagement portions that are radially inwardly projecting for a force-fitting and/or form-fitting contacting of the surgical tool for holding the surgical tool; and
      a catching base formed at an end portion of the expander holder opposite to the insertion opening, the clamping arms extending from the catching base in an axial direction toward the open front side, the catching base comprising a first flat side and a second flat side, the catching base being formed by a chamfer-free plate from which the clamping arms axially extend, the catching base forming a welding, soldering or gluing portion in a central region on at least one of the first flat side and the second flat side of the catching base; and
   B. a retaining device comprising:
      a first perforated plate having first holes for insertion of the surgical tool and first crosspieces, the first holes being separated from each other by the first crosspieces; and
      a second perforated plate having second holes and second crosspieces, the second perforated plate being spaced parallel to the first perforated plate and connected to the first perforated plate, the second holes being separated from each other by the second crosspieces,
      the second crosspieces intersecting at junction points arranged in alignment with the first holes, and the catching base of the expander holder is being firmly bonded or bondable to the junction points of the second crosspieces.

2. The tool set according to claim 1, wherein the second crosspieces at the junction points form a welding, soldering or gluing surface which is at least as large as an area of the catching base.

3. The tool set according to claim 1, wherein the second holes are rectangular and are arranged in rows offset by 60°.

4. The tool set according to claim 1, wherein an upper side of the catching base is firmly bonded or bondable to an axial side of the second perforated plate facing the first perforated plate.

5. The tool set according to claim 4, wherein the expander holder is passable through the second holes with the plurality of clamping arms through the second holes and placeable on one of the junction points against the insertion direction of the surgical tool in such a way that the catching base projects from the second perforated plate as an axial spacer against the insertion direction of the surgical tool.

6. The tool set according to claim 1, wherein the first holes of the first perforated plate each comprise a hole center, the first holes being arranged in a plurality of rows that are parallel and spaced from one another such that the hole centers in a first row of the plurality of rows are offset from the hole centers in a second row of the plurality of rows that is adjacent to the first row, said hole centers in the first row being offset from the hole centers in the second row by a crosspiece width of the second crosspieces.

7. The tool set according to claim 1, wherein the catching base has a weldable insert or a weldable coating.

8. The tool set according to claim 2, wherein the welding, soldering or gluing surface is at least as large as the welding, soldering or gluing portion of the catching base.

9. The tool set according to claim 3, wherein the second crosspieces widen in such a way that the second crosspieces curve at corner points of the second holes in a direction of a hole center.

10. The tool set according to claim 1, wherein a lower side of the catching base is firmly bonded or bondable to an axial side of the second perforated plate facing the first perforated plate.

* * * * *